(12) United States Patent
Simanzhenkov et al.

(10) Patent No.: US 11,077,430 B2
(45) Date of Patent: *Aug. 3, 2021

(54) OXIDATIVE DEHYDROGENATION CATALYST

(71) Applicant: NOVA Chemicals (International) S.A., Fribourg (CH)

(72) Inventors: Vasily Simanzhenkov, Calgary (CA); Xiaoliang Gao, Calgary (CA); David Sullivan, Calgary (CA); Hanna Drag, Calgary (CA); Leonid Modestovich Kustov, Moscow (RU); Aleksey Victorovich Kucherov, Moscow (RU); Elena Dmitrievna Finashina, Moscow (RU)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/879,976

(22) Filed: May 21, 2020

(65) Prior Publication Data

US 2020/0282383 A1    Sep. 10, 2020

Related U.S. Application Data

(60) Continuation of application No. 16/421,664, filed on May 24, 2019, now Pat. No. 10,695,754, which is a (Continued)

(30) Foreign Application Priority Data

Aug. 20, 2015 (CA) ................ CA 2900775

(51) Int. Cl.
*B01J 27/057* (2006.01)
*B01J 37/03* (2006.01)
(Continued)

(52) U.S. Cl.
CPC ......... *B01J 27/0576* (2013.01); *B01J 23/002* (2013.01); *B01J 23/28* (2013.01);
(Continued)

(58) Field of Classification Search
CPC ... B01J 37/12; B01J 23/16; B01J 23/22; B01J 23/28; B01J 27/0576; B01J 37/08;
(Continued)

(56) References Cited

U.S. PATENT DOCUMENTS

| 2,895,920 A | 7/1959 | Janoski |
| 3,474,042 A | 10/1969 | Fattore et al. |

(Continued)

FOREIGN PATENT DOCUMENTS

| EP | 0 261 264 A1 | 3/1988 |
| JP | 20001432244 A | 5/2000 |
| WO | 2009/022780 A1 | 2/2009 |

OTHER PUBLICATIONS

Wen C.Y. and Yu, Y.H.; Mechanics of Fluidization, Chemical Engineering Progress Symposium Series; Fluid Particle Technology, No. 62, vol. 62, (1966) pp. 100-111.

(Continued)

*Primary Examiner* — Patricia L. Hailey
(74) *Attorney, Agent, or Firm* — Thomas J. Styslinger

(57) ABSTRACT

Oxidative dehydrogenation catalysts comprising MoVNb-TeO having improved consistency of composition and a 25% conversion of ethylene at less than 420° C. and a selectivity to ethylene above 95% are prepared by treating the catalyst precursor with $H_2O_2$ in an amount equivalent to 0.30-2.8 mL $H_2O_2$ of a 30% solution per gram of catalyst precursor prior to calcining.

10 Claims, 3 Drawing Sheets

Related U.S. Application Data division of application No. 15/219,317, filed on Jul. 26, 2016, now Pat. No. 10,350,582.

(51) Int. Cl.

| | | |
|---|---|---|
| *B01J 37/12* | (2006.01) | |
| *B01J 35/02* | (2006.01) | |
| *C07C 5/48* | (2006.01) | |
| *B01J 37/10* | (2006.01) | |
| *B01J 23/00* | (2006.01) | |
| *B01J 23/28* | (2006.01) | |
| *B01J 35/00* | (2006.01) | |
| *B01J 37/00* | (2006.01) | |
| *B01J 37/06* | (2006.01) | |
| *B01J 37/08* | (2006.01) | |

(52) U.S. Cl.
CPC ........... *B01J 35/0026* (2013.01); *B01J 35/02* (2013.01); *B01J 37/009* (2013.01); *B01J 37/03* (2013.01); *B01J 37/06* (2013.01); *B01J 37/08* (2013.01); *B01J 37/10* (2013.01); *B01J 37/12* (2013.01); *C07C 5/48* (2013.01); *B01J 2523/00* (2013.01); *C01P 2002/70* (2013.01); *C01P 2006/10* (2013.01); *C01P 2006/90* (2013.01); *C07C 2523/20* (2013.01); *C07C 2523/22* (2013.01); *C07C 2523/28* (2013.01); *C07C 2527/057* (2013.01); *Y02P 20/52* (2015.11)

(58) Field of Classification Search
CPC .... B01J 37/086; B01J 37/088; B01J 2523/00; C07C 5/48; C07C 2523/20; C07C 2523/22; C07C 2523/28; C07C 2527/057; Y02P 20/52; C01P 2002/70; C01P 2006/10; C01P 2006/90
USPC .................. 585/654, 661, 662; 502/311, 312
See application file for complete search history.

(56) References Cited

U.S. PATENT DOCUMENTS

| | | |
|---|---|---|
| 4,708,070 A | 11/1987 | Hiltner |
| 6,642,173 B2 | 11/2003 | Bogan, Jr. |
| 6,781,008 B2 | 8/2004 | Bogan, Jr. |
| 6,867,328 B2 | 3/2005 | Borgmeier et al. |
| 7,005,403 B2 | 2/2006 | Borgmeier et al. |
| 7,038,082 B2 | 5/2006 | Borgmeier et al. |
| 7,091,377 B2 | 8/2006 | Borgmeier et al. |
| 7,214,822 B2 | 5/2007 | Borgmeier et al. |
| 8,105,972 B2 | 1/2012 | Gaffney et al. |
| 8,519,210 B2 | 8/2013 | Arnold et al. |
| 10,350,582 B2 * | 7/2019 | Simanzhenkov ........ B01J 35/02 |
| 10,695,754 B2 * | 6/2020 | Simanzhenkov ........ B01J 37/12 |
| 2015/0119622 A1 | 4/2015 | De Rooij et al. |
| 2018/0104675 A1 * | 4/2018 | Simanzhenkov ........ B01J 37/04 |
| 2018/0193827 A1 * | 7/2018 | Simanzhenkov ........ B01J 37/04 |
| 2019/0039053 A1 * | 2/2019 | Kim ..................... B01J 35/1014 |
| 2019/0240647 A1 * | 8/2019 | Gao ......................... B01J 23/22 |

OTHER PUBLICATIONS

Peri, J.B. and Hensley, A.L., Jr.; The Surface Structure of Silica Gel, The Journal of Physical Chemistry, vol. 72, No. 8, Aug. 1968, pp. 2926-2933.

Baca, M.; Pigamo, A.; Dubois, J.L. and Millet, J.M.M.; Fourier transform indrared spectroscopic study of surface acidity by pyridine adsorption on the M1 active phase of the MoVTe(Sb)NbO catalysts used in propane oxidation; Catalysis Communications 6 (2005), Available online at www.sciencedirect.com, pp. 215-220.

Nguyen, T.T.; Aouine, M. and Millet, J.M.M.; Optimizing the efficiency of MovTeNbO catalysts for ethane oxidative dehydrogenation to ethylene; Catalysis Communications 21 (2012), Journal homepage: www.elsevier.com/locate/catcom; pp. 22-26.

Havecker, Michael, Wrabetz, Sabine, Krohnert, Jutta, Csepei, Lenard-Istvan, D'Alnoncourt, Raoul Naumann, Kolen'Ko, Yury V., Girgsdies, Frank, Schlogl, Robert, and Trunschke, Annette, Surface chemistry of phase-pure M1 MoVTeNb oxide during operation in selective oxidation of propane to acrylic acid, Journal of Catalysis 285 (2012), journal homepage: www.elsevier.com/locate/jcat, pp. 48-60.

* cited by examiner

OXIDATIVE DEHYDROGENATION CATALYST

CROSS REFERENCE TO RELATED APPLICATIONS

This application is a continuation of U.S. patent application Ser. No. 16/421,664, filed on May 24, 2019, which is a divisional of U.S. patent application Ser. No. 15/219,317, filed on Jul. 26, 2016, which claims the benefit of the earlier filing date of Canadian application serial number 2,900,775 filed on Aug. 20, 2015, all of which are hereby incorporated in their entirety by reference.

The present invention relates to an improved method for making a catalyst for the oxidative dehydrogenation of lower alkanes to lower alkenes. Multicomponent metal oxide catalysts for the oxidative dehydrogenation of alkanes are known. Such catalysts are typically made by mixing solutions of metals and then precipitating the metal oxide "mixture" from the solution and calcining it. As a result, the catalysts are heterogeneous mixtures of various metal oxides and phases and may include some highly active species but also some species which have a significantly lower activity. Applicants have found that by treating the precipitated metal oxides with a controlled amount of hydrogen peroxide prior to calcining the activity of the catalyst is improved.

U.S. Pat. No. 2,895,920 issued Jul. 21, 1959 to Janoski, assigned to Sun Oil Company teaches a process to prepare a catalyst for the conversion of hydrocarbons such as dehydrogenation. The catalysts comprise oxides of cobalt, iron, nickel, molybdenum, manganese, chromium, vanadium, tin, and tungsten. The catalysts do not incorporate any niobium. In the process to make the catalysts, a hydrogel is prepared of metal oxide(s) which are difficult to reduce and metal oxides which are capable of existing in several oxidation states. A hydrogel of the metals is prepared and aged in the presence of hydrogen peroxide. The aged hydrogel is treated with a compound to precipitate the metals which are then filtered, dried and calcined. The sequence of treatments is different than that in the present invention. A hydrogel is not prepared in the process of the present invention.

U.S. Pat. No. 3,474,042 issued Oct. 21, 1969 to Fattore et al., assigned to Montecatini Edison S.p.A. teaches a metal oxide catalyst comprising molybdenum or tungsten. The catalysts are prepared by forming peroxy—compounds of tungsten and molybdenum, by reacting the metal oxide with hydrogen peroxide or compounds which form hydrogen peroxide. The molar ratio of peroxide to metal oxide may range from 0.25 to 10, typically from 1 to 3. The solution may be spray-dried or impregnated into a carrier.

U.S. Pat. No. 4,709,070 issued Nov. 24, 1987 to Sasaki et al., assigned to Nitto Chemical industry Co., Ltd. teaches a method to regenerate the activity of a complex metal oxide catalyst used for oxidation, ammoxidation and oxidative dehydrogenation of alkanes. The catalysts prior to reactivation are quite different from those herein. They contain a number of elements not present in the catalysts of the present invention such as Fe, Sb, Cu, and Co. The "deactivated" catalyst is treated with a Te compound, a Mo compound or a mixture thereof. The Te and Mo compounds may be oxides. In some instances, the Te and Mo compounds may be prepared by contacting them with $H_2O_2$ in the presence of the oxide, oxyacid, salts of oxyacids, heteropoly acids or salts thereof of molybdenum (Col. 9 lines 38-42). The patent teaches away from treating the entire catalyst precursor with $H_2O_2$.

U.S. Pat. No. 8,105,972 issued Jan. 31, 2012 to Gaffney et al. from an application filed Apr. 2, 2009, assigned to Lummus Technology Inc. teaches a catalyst for the oxidative dehydrogenation of alkanes. The catalyst is formed in a conventional manner by hydrothermal treatment of metal oxide components. The resulting catalyst is recovered, dried and calcined. Then the calcined catalyst is treated with an acid. This process teaches away from the subject matter of the present invention as it teaches a post calcining treatment. Further, the patent fails to teach treatment with $H_2O_2$.

At least one embodiment of the present invention seeks to provide an improved catalyst for oxidative dehydrogenation by treating the catalyst precursor with $H_2O_2$, prior to calcining.

In one embodiment of the invention a precursor for an oxidative dehydrogenation catalyst is prepared by the hydrothermal reaction of compounds of Mo, V, Te, and Nb and, prior to calcining, treating the precursor with $H_2O_2$.

In one embodiment, the present invention provides a method to improve the consistency of an oxidative dehydrogenation catalyst of the empirical formula (measured by PIXE):

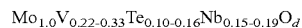

$$Mo_{1.0}V_{0.22-0.33}Te_{0.10-0.16}Nb_{0.15-0.19}O_d$$

where d is a number to satisfy the valence of the oxide comprising treating a precursor, prior to calcining, with $H_2O_2$ in an amount equivalent to 0.30-2.8 mL $H_2O_2$ of a 30% solution per gram of catalyst precursor.

In a further embodiment, the precursor is prepared by:

i) forming an aqueous solution of ammonium heptamolybdate (tetrahydrate) and telluric acid at a temperature from 30° C. to 85° C. and adjusting the pH of the solution to from 6.5 to 8.5, for example from 7 to 8, or for example from 7.3 to 7.7 with a nitrogen-containing base to form soluble salts of the metals;

ii) preparing an aqueous solution of vanadyl sulphate at a temperature from room temperature to 80° C. (for example 50° C. to 70° C., or for example 55° C. to 65° C.);

iii) mixing the solutions from steps i) and ii) together;

iv) slowly (dropwise) adding a solution of niobium monoxide oxalate ($NbO(C_2O_4H)_3$) to the solution of step iii) to form a slurry; and v) heating the resulting slurry in an autoclave under an inert atmosphere at a temperature from 150° C. to 190° C. for not less than 10 hours.

In a further embodiment, the resulting solid from step v) is filtered and washed with deionized water, and drying the washed solid for a time from 4 to 10 hours at a temperature from 70 to 100° C.

In a further embodiment, the precursor is calcined in an inert atmosphere at a temperature from 200° C. to 600° C. for a time from 1 to 20 hours.

In a further embodiment, the precursor is treated with the equivalent of from 0.3-2.8 mL of a 30% w/w solution of $H_2O_2$ per gram of catalyst precursor for a time from 5 minutes to 10 hours at a temperature from 20 to 80° C.

In a further embodiment in the catalyst, the molar ratio of Mo:V is from 1:0.22 to 1:0.29.

In a further embodiment in the catalyst, the molar ratio of Mo:Te is greater than 1:0.11 and less than 1:0.15.

In a further embodiment in the catalyst the molar ratio of Mo:V is from 1:0.22 to 1:0.25.

In a further embodiment in the catalyst, the molar ratio of Mo:Te is from 1:0.11 to 1:0.13.

In a further embodiment, the catalyst has a bulk density from 1.20 to 1.53 g/cc.

In a further embodiment in the crystalline phase of the catalyst, the amount of the phase having the formula $(TeO)_{0.39}(Mo_{3.52}V_{1.06}Nb_{0.42})O_{14}$ is above 75 wt. % of the measured crystalline phase as determined by XRD.

In a further embodiment in the crystalline phase of the catalyst, the amount of the phase having the formula $(TeO)_{0.39}(Mo_{3.52}V_{1.06}Nb_{0.42})O_{14}$ is above 85 wt. % of the measured crystalline phase as determined by XRD.

A further embodiment of the invention provides a method for the oxidative dehydrogenation of a mixed feed of ethane and oxygen in a volume ratio from 70:30 to 95:5 at a temperature less than 420° C., for example less than 400° C. at a gas hourly space velocity of not less than 500 hr$^{-1}$ and a pressure from 0.8 to 1.2 atmospheres comprising passing said mixture over the above catalyst.

In a further embodiment, a conversion to ethylene is not less than 90%.

In a further embodiment, the gas hourly space velocity is not less than 1000 hr$^{-1}$.

In a further embodiment, the calcined catalyst forms a fixed bed in the reactor.

In a further embodiment, the catalyst has the empirical formula (measured by PIXE):

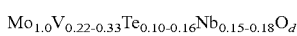

$$Mo_{1.0}V_{0.22-0.33}Te_{0.10-0.16}Nb_{0.15-0.18}O_d$$

where d is a number to satisfy the valence of the oxide and not less than 75 wt. % of a crystalline component has the formula $(TeO)_{0.39}(Mo_{3.52}V_{1.06}Nb_{0.42})O_{14}$ as determined by XRD.

In a further embodiment in the crystalline phase of the catalyst having the formula $(TeO)_{0.71}(Mo_{0.73}V_{0.2}Nb_{0.07})_3O_9$ is from 2.4 to 12 wt. % as determined by XRD.

In a further embodiment, a surface (internal) of a reactor is seeded with the above catalyst.

In a further embodiment, the surface of the reactor is selected from stainless steel, silica, alumina coating and polytetrafluoroethylene.

In a further embodiment, the reactor contains particulates (irregular such as flakes, granules, globules, filaments etc. or regular such as spheres, elliptical, rods, rectangular prisms (both right and non right), pentagonal prisms, pyramids, etc.) of stainless steel, silica, alumina and polytetrafluoroethylene seeded with the above catalyst.

In a further embodiment, there is provided a fully fluorinated ethylene propylene polymer reactor coating seeded with the above catalyst.

NUMBERS RANGES

Figure 1:
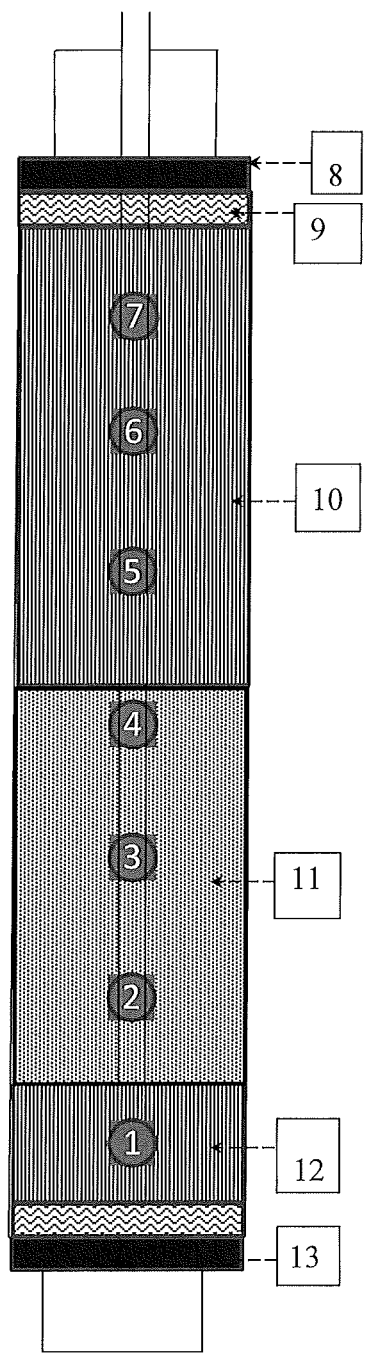
FIG. 1 is a schematic drawing of the reactor used for the testing the ODH catalysts.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

In the specification, the phrase the temperature at which there is 25% conversion of ethane to ethylene is determined by plotting a graph of conversion to ethylene against temperature typically with data points below and above 25% conversion. Then a plot of the data is prepared or the data is fit to an equation and the temperature at which there is a 25% conversion of ethane to ethylene is determined. In some instances in the examples the data had to be extrapolated to determine the temperature at which 25% conversion occurred.

In the specification, the phrase selectivity at 25% conversion is determined by plotting the selectivity as function of temperature. The data is then plotted on a graph of selectivity against temperature or fit to an equation. Then having calculated the temperature at which 25% conversion occurs one can determine either from the graph or from the equation the selectivity at that temperature.

In some embodiments the calcined catalysts of the present invention have the formula:

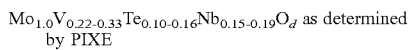

$$Mo_{1.0}V_{0.22-0.33}Te_{0.10-0.16}Nb_{0.15-0.19}O_d \text{ as determined by PIXE}$$

where d is a number to satisfy the valence of the oxide. In some embodiments the molar ratio of Mo:V in the calcined catalyst is from 1:0.22 to 1:0.33, in other embodiments the molar ratio of Mo:V in the calcined catalyst is from 1:0.22 to 1:0.29, in some embodiments from 1:0.22 to 1:0.25. In other embodiments the molar ratio of Mo:Te in the calcined catalyst is greater than 1:0.10 and less than 1:0.16, in further embodiments the molar ratio of Mo:Te in the calcined catalyst is from 1:0.11 to 1:0.15.

The catalyst precursor may be prepared by mixing solutions or slurries (suspensions) of oxides or salts of the metallic components.

In some embodiments, the precursor may be prepared by a process comprising the following steps:

i) forming an aqueous solution of ammonium heptamolybdate (tetrahydrate) and telluric acid at a temperature from 30° C. to 85° C. and adjusting the pH of the solution to 6.5 to 8.5, for example from 7 to 8, or for example from 7.3 to 7.7 (in one embodiment preferably with a nitrogen-containing base to form soluble salts of the metals);

ii) preparing a aqueous solution of vanadyl sulphate at a temperature from room temperature to 80° C. (for example 50° C. to 70° C., or for example 55° C. to 65° C.);

iii) mixing the solutions from steps i) and ii) together;

iv) slowly (dropwise) adding a solution of niobium monoxide oxalate ($NbO(C_2O_4H)_3$) to the solution of step iii) to form a slurry;

v) heating the resulting slurry in an autoclave under an inert atmosphere at a temperature from 150° C. to 190° C. for not less than 10 hours.

In a further embodiment, the slurry from step v) is filtered, washed with deionized water and dried for a time from 4 to 10 hours at a temperature from 70 to 100° C.

In a further embodiment:
following step i) one or more of the following steps may be incorporated in the process:

a) evaporating the aqueous solvent to obtain a solid;

b) drying the solid at a temperature from 80° C. to 100° C.; and c) redissolving the solid in water at a temperature from 40° C. to 80° C. (for example 50° C. to 70° C., or for example 55° C. to 65° C.).

In a further embodiment following step ii) the solutions are cooled to a temperature from 20° C. to 30° C.

In a further embodiment as a part of step vi) the solution is cooled to a temperature from 20° C. to 30° C.

In a further embodiment, the precursor may be made by a process comprising:

i) forming an aqueous solution of ammonium heptamolybdate (tetrahydrate) and telluric acid at a temperature from 30° C. to 85° C. and adjusting the pH of the solution to 7.3 to 7.7 (for example 7.4 to 7.5) with a nitrogen-containing base to form soluble salts of the metals;

ii) evaporating the aqueous solvent to obtain a solid;

iii) drying the solid at a temperature from 80° C. to 100° C.;

iv) redissolving the solid in water at a temperature from 40° C. to 80° C. (for example 50° C. to 70° C., or for example 55° C. to 65° C.);

v) preparing a aqueous solution of vanadyl sulphate at a temperature from room temperature to 80° C. (for example 50° C. to 70° C., or for example 55° C. to 65° C.);

vi) cooling the solutions from steps iv) and v) to a temperature from 20 to 30° C.

vii) mixing the cooled solutions from step vi together;

viii) slowly (dropwise) adding a solution of niobium monoxide oxalate ($NbO(C_2O_4H)_3$) to the solution of step vii) to form a (brown) slurry;

ix) heating the resulting slurry in an autoclave under an atmosphere free of oxygen at a temperature from 150° C. to 190° C. for not less than 10 hours;

x) cooling the autoclave to room temperature and filtering and washing with deionized water the resulting solid; and xi) drying the washed solid for a time from 4 to 10 hours at a temperature from 70 to 100° C.

In some embodiments, the (catalyst) reactor may be lined with a coating selected from stainless steel, silica, alumina coating and polytetrafluoroethylene, preferably polytetrafluoroethylene (TEFLON) seeded with catalyst having a 25% conversion to ethylene at 420° C. or less and a selectivity to ethylene of not less than 90%.

The seed catalyst may be a catalyst having the empirical formula (measured by PIXE):

$$Mo_{1.0}V_{0.22-0.33}Te_{0.10-0.16}Nb_{0.15-0.18}O_d$$

where d is a number to satisfy the valence of the oxide and having not less than 75 wt. % of a crystalline component of the formula $(TeO)_{0.39}(Mo_{3.52}V_{1.06}Nb_{0.42})O_{14}$ as determined by XRD.

In some embodiments, the (catalyst precursor) reactor may be lined with a coating of a fully fluorinated ethylene propylene polymer (FEP) seeded with a catalyst having a 25% conversion to ethylene at 420° C. or less and a selectivity to ethylene of not less than 90%.

In some embodiments, the seed catalyst has the empirical formula (measured by PIXE) $Mo_{1.0}V_{0.22-0.33}Te_{0.10-0.16}Nb_{0.15-0.18}O_d$ where d is a number to satisfy the valence of the oxide and having not less than 75 wt. % of a crystalline component of the formula $(TeO)_{0.39}(Mo_{3.52}V_{1.06}Nb_{0.42})O_{14}$ as determined by XRD.

The seed catalyst loadings may range from 1 to 15 wt. % of the surface of the reactor (e.g. steel, TEFLON or FEP).

In some instances, the (catalyst precursor) reactor contains particulates of stainless steel, silica, alumina and polytetrafluoroethylene seeded with a catalyst having a 25% conversion to ethylene at 420° C. or less and a selectivity to ethylene of not less than 90%.

In some embodiments, the seed catalyst has the empirical formula (measured by PIXE) $Mo_{1.0}V_{0.22-0.33}Te_{0.10-0.16}Nb_{0.15-0.19}O_d$ where d is a number to satisfy the valence of the oxide and having not less than 75 wt. % of a crystalline component of the formula $(TeO)_{0.39}(Mo_{3.52}V_{1.06}Nb_{0.42})O_{14}$ as determined by XRD.

The particulates may be (irregular such as flakes, granules, globules, filaments etc. or regular such as spheres, elliptical, rods (stirring bars), rectangular prisms (both right and non-right), pentagonal prisms, pyramids, etc.) The seed catalyst loadings on the particulates may range from 1 to 15 wt. % of the particulates.

In some circumstances, it may be easier to replace particulates on which the seed catalyst has, for whatever reason, been depleted with new seed particles having an appropriate loading of seed particles than to replenish the seed coating on the interior surface of the catalyst reactor.

In some embodiments, the catalyst produced from a hydrothermal reactor seeded with catalyst having a 25% conversion to ethylene at 420° C. or less and a selectivity to ethylene of not less than 90% has the empirical formula as determined by PIXE, $Mo_1V_{0.34-0.39}Te_{0.09-0.14}Nb_{0.14-0.16}O_d$ where d is a number to satisfy the valence of the oxide.

The peroxide treatment may take place at atmospheric pressure and room temperature (e.g. from 15° C. to 30° C.) to about 80° C., in some instances from 35° C. to 75° C. in other instances from 40° C. to 65° C. The peroxide has a concentration from 10 to 30 wt. %, in some instances from 15 to 25 wt. %. The treatment time may range from 1 to 10 hours, in some cases from 2 to 8 hours, in other cases from 4 to 6 hours.

The catalyst precursor is treated with the equivalent of from 0.3-2.8, in some embodiments from 0.3-2.5 mL of a 30 wt. % solution of aqueous $H_2O_2$ per gram of precursor. The treatment should be in a slurry (e.g. the precursor is at least partially suspended) to provide an even distribution of $H_2O_2$ and to control the temperature rise. For post calcination treatment with $H_2O_2$ there is a sudden delayed violent reaction with $H_2O_2$. The process of the present invention is an instantaneous reaction which is more controlled and safer.

The treated catalyst precursor is then subject to calcining to produce the active oxidative dehydrogenation catalyst. The treated precursor may be calcined in an inert atmosphere at a temperature from 200° C. to 600° C. for a time from 1 to 20 hours. The purge gases used for calcining are inert gases, including one or more of nitrogen, helium, argon, $CO_2$ (preferably high purity >90%), said gases or mixture containing less than 1 vol.-% hydrogen or air, at 200-600° C., or for example at 300-500° C. The calcining step may take from 1 to 20, in some instances from 5 to 15 in other instances from about 8 to 12 hours, for example about 10 hours. The resulting mixed oxide catalyst is a friable solid, in some embodiments the solid is insoluble in water. In some embodiments the calcined product has a bulk density from 1.20 to 1.53 g/cc. This bulk density is based on how much 1.5 mL of pressed and crushed catalyst weighs.

The resulting oxidative dehydrogenation catalyst is heterogeneous. It has an amorphous component and a crystalline component. The elemental analysis of the catalyst may be determined by any suitable technique. One useful technique is Particle Induced X-Ray Emission analysis (PIXE). From a PIXE analysis of the catalyst precursor prior to treatment and after treatment with $H_2O_2$ it is determined that the empirical molar ratio of Mo to V decreases, for example, from 1:0.33 to 1:0.40 to from 1:0.22 to 1:0.33, in some instances from 1.0:0.22 to 1.0:0.25 compared to a calcined material which has not been treated with hydrogen peroxide. Further it is found that, in some embodiments, the molar ratio of Mo:Te is tightened and increased (over the base catalyst) from a range from 1:0.03 to 1:0.13 to greater than 1:0.10 and less than 1:0.16, in some instances from 1.0:0.11 to 1:0 to 0.15 compared to a calcined oxidative dehydrogenation catalyst which has not been so treated.

The catalyst has one or more crystalline components and an amorphous component. The crystalline component may be analyzed using X-Ray diffraction (XRD). There are a number of suppliers of X-Ray diffractometers including Rigaku Shimadzu, Olympus and Bruker. A powder sample is irradiated with X-Rays. The X-Rays given off from the sample pass through a diffraction grid and are collected in a goniometer (recorder). The results may be analyzed using a computer program (for example one provided by the instrument supplier) and compared to a data base (International Center for Diffraction Data ICDD) using a computer to determine the composition of the crystalline phase(s).

The 2θ X-Ray diffraction pattern has a ratio of peak height at 2θ from 0 to 20° to maximum peak height of less than 15%, in some instances less than 10%.

The crystalline phase of the catalyst is also heterogeneous. The X-Ray diffraction results may be analyzed by computer programs to identify various likely crystalline species and their relative amounts compared to the structures in a data base (e.g., deconvoluted).

In some embodiments, the crystalline phase includes the following crystalline species:

$(Mo_{0.6}Nb_{0.22}V_{0.18})_5O_{14}$;
$TeO_{0.71}(Mo_{0.73}V_{0.2}Nb_{0.07})_3O_9$;
$(TeO)_{0.39}(Mo_{3.52}V_{1.06}Nb_{0.42})O_{14}$;
$V_{1.1}Mo_{0.9}O_5$; $Mo_4V_6O_{25}$; and
$VOMoO_4$ X-Ray diffraction analysis of the precursor and the calcined catalyst shows treatment results in a change in the composition of the crystalline phase. The treatment in accordance with the present invention increases the phase of the crystalline component having the empirical formula $(TeO)_{0.39}(Mo_{3.52}V_{1.06}Nb_{0.42})$ to not less than 75 wt. %, in some instances not less than 85 wt. %, in some instances not less than 90 wt. %, in some instances not less than 95 wt. % of the of the crystalline phase.

In some embodiments, the phase of the crystalline component having the empirical formula $TeO_{0.71}(Mo_{0.73}V_{0.2}Nb_{0.07})_3O_9$ is present in an amount of from about 2.4 to 12 wt. %, in some embodiments the phase is present in amounts less than about 8 wt. %, in further embodiments less than 3.5 wt. %.

The calcined catalyst product is a dry friable product, which in some embodiments is insoluble in water. If required the catalyst may be subject to a sizing step, such as grinding, to produce a desired particle size. Depending on how the catalyst is to be used the particle size may be different. For example for spray drying with a support the particle size may range from about 5 to 75 μm, in some cases from 10 to 60 μm. For use in a bed in unsupported form the particles may have a size from about 0.1 to 0.5 mm in some instances from 0.2 to 0.4 mm.

In the present invention, the feed to the oxidative dehydrogenation reactor includes oxygen in an amount below the upper explosive/flammability limit. For example for ethane oxidative dehydrogenation, the oxygen will be present in an amount of, for example, not less than about 16 mole %, or for example, about 18 mole %, or for example from about 22 to 27 mole %, or 23 to 26 mole %. It is desirable not to have too great an excess of oxygen as this may reduce selectivity arising from combustion of feed or final products. Additionally too high an excess of oxygen in the feed stream may require additional separation steps at the downstream end of the reaction.

To maintain a viable fluidized or moving bed, the mass gas flow rate through the bed must be above the minimum flow required for fluidization, and, for example, from about 1.5 to about 10 times $U_{mf}$, for example, from about 2 to about 6 times $U_{mf}$. $U_{mf}$ is used in the accepted form as the abbreviation for the minimum mass gas flow required to achieve fluidization, C. Y. Wen and Y. H. Yu, "Mechanics of Fluidization", Chemical Engineering Progress Symposium Series, Vol. 62, p. 100-111 (1966). In some instances the superficial gas velocity required ranges from 0.3 to 5 m/s.

The reactor may also be a fixed bed reactor.

The oxidative dehydrogenation process comprises passing a mixed feed of ethane and oxygen at a temperature less than 420° C. in some instances less than 410° C., in some instances less than 400° C., in some instances less than 390° C., in some instances less than 380° C., in some instances as low as 375° C., at a gas hourly space velocity of not less than 500 hr$^{-1}$, for example, not less than 1000 hr$^{-1}$, or for example, not less than 2800 hr$^{-1}$, or for example, at least 3000 hr$^{-1}$ through one or more beds and a pressure from 0.8 to 1.2 atmospheres comprising passing said mixture over the oxidative dehydrogenation catalyst. In some embodiments the oxidative dehydrogenation reactor operates at temperatures below 400° C., or for example from 375° C. to 400° C.

The outlet pressure from the reactor may be from 105 kPa (15 psi) to 172.3 kPa (25 psi) and the inlet pressure is higher by the pressure drop across the bed which depends on a number of factors including reactor configuration, particle size in the bed and the space velocity. The pressure drop may be below 689 kPa (100 psi), for example, less than 206.7 kPa (30 psi).

The residence time of one or more alkanes in the oxidative dehydrogenation reactor is from 0.002 to 20 seconds.

The Support/Binder:

If required there are several ways the oxidative dehydrogenation catalyst may be supported or bound.

Example components for forming ceramic supports and for binders include oxides of titanium, zirconium, aluminum, magnesium, silicon, phosphates, boron phosphate, zirconium phosphate and mixtures thereof, for both fluidized and fixed bed reactors. In the fluidized bed catalyst may be spray dried with the binder, forming spherical particles ranging in size (effective diameter) from 40-100 μm. However, one needs to be careful to insure that particles area is sufficiently robust to minimize the attrition in the fluidized bed.

The support for the catalyst for the fixed bed may further be a ceramic precursor formed from oxides, dioxides, nitrides, carbides selected from silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, yttrium oxide, aluminum silicate, silicon nitride, silicon carbide and mixtures thereof.

In one embodiment, the support for the fixed bed may have a low surface area less than 20 $m^2/g$, alternatively, less than 15 $m^2/g$, in some instances, less than 3.0 $m^2/g$ for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 $m^2/g$.

The low surface area support could be of any conventional shape such as spheres, rings, saddles, etc.

It is important that the support be dried prior to use (i.e. before adding catalyst). The support may be heated at a temperature of at least 200° C. for up to 24 hours, for example at a temperature from 500° C. to 800° C. for about 2 to 20 hours, or for example 4 to 10 hours. The resulting support will be free of adsorbed water and should have a surface hydroxyl content from about 0.1 to 5 mmol/g of support, for example from 0.5 to 3 mmol/g.

The amount of the hydroxyl groups on silica may be determined according to the method disclosed by J. B. Peri and A. L. Hensley, Jr., in J. Phys. Chem., 72 (8), 2926, 1968, the entire contents of which are incorporated herein by reference.

The dried support for a fixed bed catalyst may be compressed into the required shape by compression molding. Depending on the particle size of the support, it may be combined with an inert binder to hold the shape of the compressed part.

Loadings

In some embodiments the catalyst loading on the support for a fixed bed catalyst provides from 1 to 30 weight %, for example from 5 to 20 weight %, or for example from 8 to 15 weight % of said catalyst and from 99 to 70 weight %, or for example from 80 to 95 weight %, or for example from 85 to 92 weight %, respectively, of said support.

The catalyst may be added to the support in any number of ways. For example, the catalyst could be deposited from an aqueous slurry onto one of the surfaces of the low surface area support by impregnation, wash-coating, brushing or spraying. The catalyst could also be co-precipitated from a slurry with the ceramic precursor (e.g. alumina) to form the low surface area supported catalyst.

The catalyst loading for the fluidized bed may be chosen based on a number of factors including the volume of bed, the flow rate of alkane through the bed, energy balance in the bed, binder type, etc. For the fluidized bed catalyst loading may cover a wide range of values ranging from 10 wt. % up to 90 wt. %, or for example above 20 wt. %, or for example above 35 wt. %.

The process should be operated to have a conversion of ethane to ethylene of at least 90%, in some instances 95%, desirably greater than 98% and a selectivity to ethylene of not less than 95%, in some instances greater than 97%.

The Oxidative Dehydroqenation Processes

The catalyst of the present invention may be used with a fluidized bed or a fixed bed exothermic reaction. The fixed bed reactor is a tubular reactor and in further embodiment the fixed bed reactor comprises multiple tubes inside a shell (e.g. a shell and tube heat exchanger type construction). In a further embodiment the fixed bed reactor may comprise a number of shells in series and/or parallel. The reactions may involve one or more dehydrogenation steps including oxidative dehydrogenation, and hydrogen transfer steps including oxidative coupling of a hydrocarbon.

In some embodiments, these reactions are conducted at temperatures from about 375° C. up to about 410° C., at pressures from about 100 to 21,000 kPa (15 to 3000 psi), at, for example, an outlet pressure from rom 105 kPa (15 psi) to 172.3 kPa (25 psi), in the presence of an oxidative dehydrogenation catalyst. The hydrocarbon stream may contain a range of compounds including $C_{2-4}$ aliphatic hydrocarbons.

In some embodiments, the reactions include the oxidative coupling of aliphatic hydrocarbons, for example $C_{1-4}$ aliphatic hydrocarbons particularly methane (e.g. when the ethane stream contains some methane) and the oxidative dehydrogenation of $C_{2-4}$ aliphatic hydrocarbons. Such reactions may be conducted using a mixed feed of hydrocarbons, in some embodiments methane or ethane or both and oxygen in a volume ratio from 70:30 to 95:5 at a temperature less than 420° C., for example less than 400° C. at a gas hourly space velocity of not less than 280 $hr^{-1}$, in some embodiments not less than 500 $hr^{-1}$, or not less than 1000 $hr^{-1}$, or for example not less than 2800 $hr^{-1}$, or for example at least 3000 $hr^{-1}$, and a pressure from 0.8 to 1.2 atmospheres. In some embodiments the process may have an overall conversion of from about 50 to about a 100%, or from about 75 to 98% and a selectivity to ethylene of not less than 90%, in some instances not less than 95%, in further embodiments not less than 98%. In some cases the temperature upper control limit is less than about 400° C., in some embodiments less than 385° C.

The resulting product stream is treated to separate ethylene from the rest of the product stream which may also contain co-products such as acetic acid, and un-reacted feed which is recycled back to the reactor.

Separation

The product stream from the reactor should have a relatively low content of ethane less, than 20 wt. %, in some cases less than 15 wt. % in some cases less than 10 wt. %. Additionally, the product stream should have a low content of by products such as water, carbon dioxide, and carbon monoxide, for example cumulatively in a range of less than 5 wt. %, or for example less than 3 wt. %.

The feed and by products may need to be separated from the product stream. Some processes may use so called dilute ethylene streams. For example if the product stream does not contain too much ethane, for example less than about 15 vol. % the stream may be used directly without further purification in a polymerization reactor such as a gas phase, slurry or solution process.

The most common technique would be to use a cryogenic C2 splitter. Other known ethylene/ethane separation techniques could also be used including adsorption (oil, ionic liquids and zeolite).

The present invention will now be illustrated by the following non limiting examples.

In the examples the fixed bed reactor unit used for the oxidative dehydrogenation reaction is schematically shown in FIG. 1. The reactor was a fixed bed stainless steel tube reactor having a 2 mm (¾") outer diameter and a length of 117 cm (46 inches). The reactor is in an electrical furnace sealed with ceramic insulating material. There are 7 thermocouples in the reactor indicated at numbers 1 through 7. Thermocouples are used to monitor the temperature in that zone of the reactor. Thermocouples 3 and 4 are also used to control the heating of the reactor bed. The feed flows from the top to the bottom of the reactor. At the inlet there is a ceramic cup 8 to prevent air drafts in the reactor. Below the ceramic cup is a layer of quartz wool 9. Below the layer of quartz wool is a layer of catalytically inert quartz powder. Below the quarts powder is the fixed bed 10 comprising catalyst. Below the fixed bed is a layer of quartz powder 11, a layer of quartz wool 12 and a ceramic cup 13. At the exit of the bed was a gas analyzer to determine the composition of the product stream. The GHSV was 2685 hr$^{-1}$ and the pressure was ambient.

For the examples the bed temperature was taken as an average of the temperatures from thermocouples 2, 3 and 4. The feed stream was assumed to have the same temperature as the bed.

The Nature of the Problem

Baseline Experiments

Two different base line catalysts were prepared in geographically separated laboratories.

Laboratory one used a TEFLON® lined reactor for the hydrothermal treatment which had on its surface crystals of effective catalyst prepared previously.

The formation of the pre catalyst in glassware procedure was as follows: $(NH_4)_6Mo_6TeO_{24}\cdot xH_2O$ (6.4069 g) was added to 20 mL of distilled water in a 100 mL glass beaker and stirred on a warm water bath (80° C.). $VOSO_4\times H_2O$ (3.6505 g) was dissolved in 10 mL of distilled water in a 50 mL beaker at room temperature. The $VOSO_4$ solution was poured into the $(NH_4)_6Mo_6TeO_{24}$ solution and a brown solution resulted immediately (Solution 1).

$H_3[NbO(C_2O_4)_3]\cdot 7.5H_2O$ (2.3318 g) was dissolved in 10 mL of warm water and added under air atmosphere to the Solution 1. A dense dark brown-gray colored slurry formed, which was stirred for 10 minutes under air atmosphere.

Hydrothermal Treatment

Samples of the slurry were then heated in an autoclave having a TEFLON liner seeded with prior produced catalyst under an inert atmosphere at a temperature from 150° C. to 190° C. for not less than 10 hours. The slurry was filtered, washed with deionized water and dried for a time from 4 to 10 hours at a temperature from 70 to 100° C.

The base line catalyst subsamples were immediately calcined.

Two samples were prepared in this manner.

One sample (A) had a 25% conversion of ethane to ethylene at about 370° C. and a selectivity at this temperature of 98%.

The second sample (B) had a 25% conversion of ethane to ethylene at about 354° C. and a selectivity at this temperature of 99%.

This shows even with catalyst seeds in the hydrothermal treatment there is variability. (This may be due to differences in the seed crystals.)

Three subsamples of precatalyst A and four subsamples of precatalsyt B were treated with various amounts of $H_2O_2$ then calcined and then used to oxidatively dehydrogenate a mixture of 78% ethane and 22% oxygen at a flow rate of 600 cm³/h.

The results are set forth in Table 1 below.

TABLE 1

| Catalyst (Teflon) | Amount of 30 wt. % of $H_2O_2$ per 1.41 g of catalyst precursor (mL) | Temperature at which 25% conversions is reached, ° C. | Selectivity at 25% conversion, % |
|---|---|---|---|
| 1A | 5.6 | 420 | 96 |
| 2A | 2.8 | 385 | 98 |
| 3A | 2.6 | 365 | 99 |
| 1B | 3.5 | 405 | 98 |
| 2B | 2.0 | 365 | 98 |
| 3B | 1.5 | 370 | 99 |
| 4B | 0.8 | 360 | 99 |

Treatment of a catalyst having 25% conversion at temperatures below 420° C. and high selectivity with 30% hydrogen peroxide in amounts from 0.3 to 2.8 mL per gram of catalyst does not provoke a measurable performance loss.

Second Laboratory

Precatalyst Preparation $(NH_4)_6Mo_6TeO_{24}\cdot xH_2O$ (6.4 g) was dissolved in 20 mL of water in a 100 mL round-bottomed flask with the aid of a warm water bath. The clear solution was cooled to room temperature. $VOSO_4\times3.47H_2O$ (3.4 g) was dissolved in 10 mL of water in a 30 mL beaker (also with the aid of a warm water bath). The blue solution formed was cooled to room temperature. The $VOSO_4$ solution was poured into the $(NH_4)_6Mo_6TeO_{24}$ solution. The beaker was rinsed with water (2×0.5 mL), and the rinsing solution was added to the flask. A brown solution formed was bubbled with nitrogen and was stirred for 10 minutes. An aqueous solution of $H_3[NbO(C_2O_4)_3]$ (0.3431 mmol/g solution, 13.29 g, 4.56 mmol of Nb) was added slowly to the above brown solution with a pipette (in ~2.5 minutes). A dull red stone colored slurry formed, which was stirred with bubbling of $N_2$ for about 10 minutes.

Hydrothermal Treatment in an Unseeded TEFLON Lined Reactor

The slurry was transferred to 60 mL autoclave having a clean Teflon liner, which was degassed and refilled with $N_2$ (ambient pressure). The autoclave was heated with a heating sleeve with the content magnetically stirred (300 rpm). The mixture was heated at 175° C. internal temperature for 48 hours. The autoclave was cooled to room temperature and the content was filtered and washed with 500 mL of water. The cake was dried at 90° C. overnight, ground and sieved through 250 micron sieve. The purple solid was calcined at 600° C. (02 level in nitrogen stream: 0.4 ppm). This catalyst appeared brown in color after calcining.

The catalyst was tested as above.

The ODH reaction was carried out at temperatures up to 420° C. to avoid auto ignition temperature of the feed gas.

The conversion was low and the graph of conversion as a function of temperature had to be extrapolated linearly to get a rough estimate of the temperature at which there was 25% conversion. The estimated temperature at which there was 25% conversion was 635° C. This would not be commercially viable as it is significantly above the auto ignition temperature of a feed gas comprising 82% ethane and 18% oxygen.

Seeded TEFLON Lined Reactor

At the second laboratory the procatalyst was prepared using the following general procedure.

The procedure to prepare catalyst was as follows.

A slurry prepared as above, was poured into a 300 mL autoclave having a TEFLON liner. The reactor was dedicated and not washed between hydrothermal treatments and it had residual crystals of catalyst made during its prior use. The autoclave was closed. The head space was purged of oxygen with $N_2$ (20 psi). After purging the valve was closed and the autoclave was put in an oven at 23° C. The temperature was raised to 175° C. and held without stirring at this temperature for 50 hours. The autoclave was taken out of the oven and cooled to room temperature. The pressure of the autoclave was released through a water bubbler. The autoclave was opened. The solid was filtered, rinsed with 500 mL of water and was dried at 80° C. overnight. The brown solid (6.19 g) was loaded in a quartz boat and was calcined under a slow stream (30 mL/min) of purified nitrogen (RT to 600° C., 4 hours, 600° C. kept for 2 hours). The solid obtained was a black powder, which was ground and sieved through a 250 micron sieve (5.94 g). The resulting solid was loose (fluffy).

The catalyst was tested in the ODH reactor using the above conditions From the experiments the temperature at which there was 25% conversion to ethylene ranged from 370° C. to 383° C. and a selectivity at these temperatures was greater than 90%. This is fairly tight considering the heterogeneous nature of the catalyst and the complexity of crystalline phases and consistently below the auto ignition temperature of the feed.

The nature of the nucleation sites was not clear. It is believed if the sites comprise catalyst having a 25% conversion below 400° C. and selectivity to ethylene at this temperature above 95% the resulting catalyst has a higher probability of the resulting catalyst having these properties.

A number of samples of catalyst prepared as above in a seeded TEFLON lined hydrothermal reactor were subject to XRD analysis as described in the examples below to determine the crystalline phases in the catalyst. The results are presented in the following table.

| Phase | Sample A | Sample B | Sample C | Sample D |
|---|---|---|---|---|
| $(Mo_{0.6}Nb_{0.22}V_{0.18})_5O_{14}$ | 3.0 | 0.0 | 8.2 | 7.0 |
| $(TeO)_{0.71}(Mo_{0.73}V_{0.2}Nb_{0.07})_3O_9$ | 9.2 | 0.0 | 10.3 | 11.4 |
| $(TeO)_{0.39}(Mo_{3.52}V_{1.06}Nb_{0.42})O_{14}$ | 86.5 | 100.0 | 77.8 | 80.7 |
| $VOMoO_4$ | 1.3 | 0.0 | 3.7 | 0.9 |

This shows that even if the reactor wall (TEFLON liner or steel) in the hydrothermal reactor is seeded with catalyst there can be a significant variability in the final catalyst.

The samples of calcined catalyst obtained from a seeded reactor have the following empirical formula as determined by PIXE: $Mo_1V_{0.34-0.39}Te_{0.09-0.14}Nb_{0.14-0.16}O_d$ where d is a number to satisfy the valence of the oxide. The samples had a 25% conversion at a temperature from 372° C. to 383° C. and a selectivity to ethylene at these temperatures from 93 to 96%.

In the Second Laboratory

A series of catalysts were prepared in a clean glassware reactor and subject to hydrothermal treatment in a stainless steel reactor without a TEFLON liner and without any catalyst seeding.

General Reaction Step:

$(NH_4)_6Mo_6TeO_{24-x}H_2O$ (19.2086 g, 15.15 mmol, 1.00 molar equivalents) was dissolved in 60 mL of distilled water in a 500 mL round-bottomed flask with the aid of a warm water bath. The resulting clear and colorless solution was allowed to cool to room temperature. $VOSO_4 \times 3.47H_2O$ (10.2185 g, 62.59 mmol, 4.13 molar equivalents) was dissolved in 25 mL of distilled water in a 30 mL beaker with the aid of a warm water bath. The resulting clear blue solution formed was cooled to room temperature.

The $VOSO_4$ solution was poured into the $(NH_4)_6Mo_6TeO_{24}$ solution and a brown solution resulted immediately. The beaker which contained the $VOSO_4$ solution was rinsed with two 1 mL aliquots of water and these rinsings were added to the flask. The resulting brown solution was stirred under addition of bubbling nitrogen for 15 minutes. Aqueous $H_3[NbO(C_2O_4)_3]$ (0.3420 mmol(Nb)/g(solution), 39.9737 g(solution), 13.68 mmol(Nb), 0.903 molar equivalents) was added slowly (dropwise over seven minutes) under $N_2$ bubbling to the brown solution via a pipette. A dull purple colored slurry formed, which was stirred with bubbling of $N_2$ for 10 minutes.

General Hydrothermal Treatment Step:

The slurry was poured to a 600 mL bare steel autoclave which contained a TEFLON stir bar. The autoclave was closed and the atmosphere inside of the autoclave was evacuated (vacuum) and filled with $N_2$ (30 psi from bulk nitrogen line) 10 times, followed by an additional 10 repeats of purging with $N_2$ (30 psi from bulk nitrogen line) and releasing of $N_2$ pressure (positive pressure relief) to a water bubbler. The autoclave was left under ambient pressure of $N_2$ atmosphere and the vessel was sealed using a needle valve on the autoclave head.

The autoclave was put into a heating blanket setup, where the heat is controlled by heat controller via thermocouples inside and outside the autoclave. The heating blanket and autoclave were wrapped in thermal insulating ceramic fiber tape to ensure proper insulation. The temperature was raised to 173° C. over the period of an hour and the reaction was let to proceed, with the addition of stirring, at this temperature for 48 hours.

The autoclave was then cooled to room temperature slowly without stirring. Once cooled, the excess pressure that built up during the process of the reaction inside the autoclave was release through a water bubbler and the autoclave was opened. The solid (deep purple color) was filtered, rinsed with approximately 300 mL of distilled water (filtrate vibrant blue color) and was dried in an oven at 90° C. overnight.

General Calcination Step:

The dried catalyst solids were ground using a mortar/pestle and sieved through a 250 micron porosity sifter. The less than 0.25 micron particle size dark purple solid was loaded in a quartz boat and the boat was placed into glass furnace tube which is used for calcination. To ensure the exclusion of air during the calcination, the setup was purge under nitrogen. The calcination proceeded under a slow stream (30 mL/min) of purified nitrogen (vent through water bubbler) under the following conditions: RT to 600° C. in 4 hours and held at 600° C. for 2 hours. The solid obtained was a black powder, which was ground and sieved through a 250 micron sieve resulting in a powder that was loose and fluffy.

The catalysts were tested as above. The temperature at which 25% conversion (either measured or linearly extrapolated) ranged from 380 to 504° C. This was a broad spread in 25% conversion temperature as there was no obvious difference between the preparations. Of the five samples two had a 25% conversion temperature below 400° C. which was felt to be a "reasonable" ceiling temperature for a large scale commercial ODH reactor.

These examples further illustrate the variability in manufacturing catalysts having a 25% conversion below 400° C. absent catalyst seed having the desired properties (temperature at which there is 25% conversion less than 400° C. and a selectivity for ethylene at this temperature of greater than 90%).

In the literature it is known (Catalysis Communications 2005, 6, 215-220; Catalysis Communications 2012, 21, 22-26; Journal of Catalysis 2012, 285, 48-60) to treat ODH catalyst post calcining with hydrogen peroxide to improve performance.

In the second lab a sampled of the catalyst prepared as above catalyst was calcined at 600° C. for from 2 to 4 hours. The calcined sample was then treated with about 12 to 16 mL of 30% w/w $H_2O_2$ aqueous solution per gram of catalyst. The reaction was inconsistent in that there was no indication of reaction (e.g. no heat or bubbling) or the incubation period to start the reaction was extremely unpredictable (e.g. 20 minutes to 3 hours) and when it started the reaction was extremely fast (in seconds) and violent (potentially explosive).

The addition of $H_2O_2$ post calcination of the catalyst is not a commercially viable route to catalyst preparation due to the complication described above and safety implications First Laboratory In the first lab portions of the baseline catalyst precursor prepared with a seeded TEFLON liner were treated with up to 5.6 ml of 30% w/w $H_2O_2$ aqueous solution per gram of precursor prior to calcining. The treatment of the precursor resulted in an immediate, controlled and observable reaction (bubbling and mild heating which never exceeded about 60° C.). The treated precursor was then calcined in the normal manner.

The catalysts were then tested in the ODH reactor.

Treatment causes a minor variation of the selectivity (between 99% and 98%) up to the peroxide amount 3.5 cc, and only the use of a larger $H_2O_2$ excess (5.6 cc) provokes a measurable selectivity loss.

Figure 2:
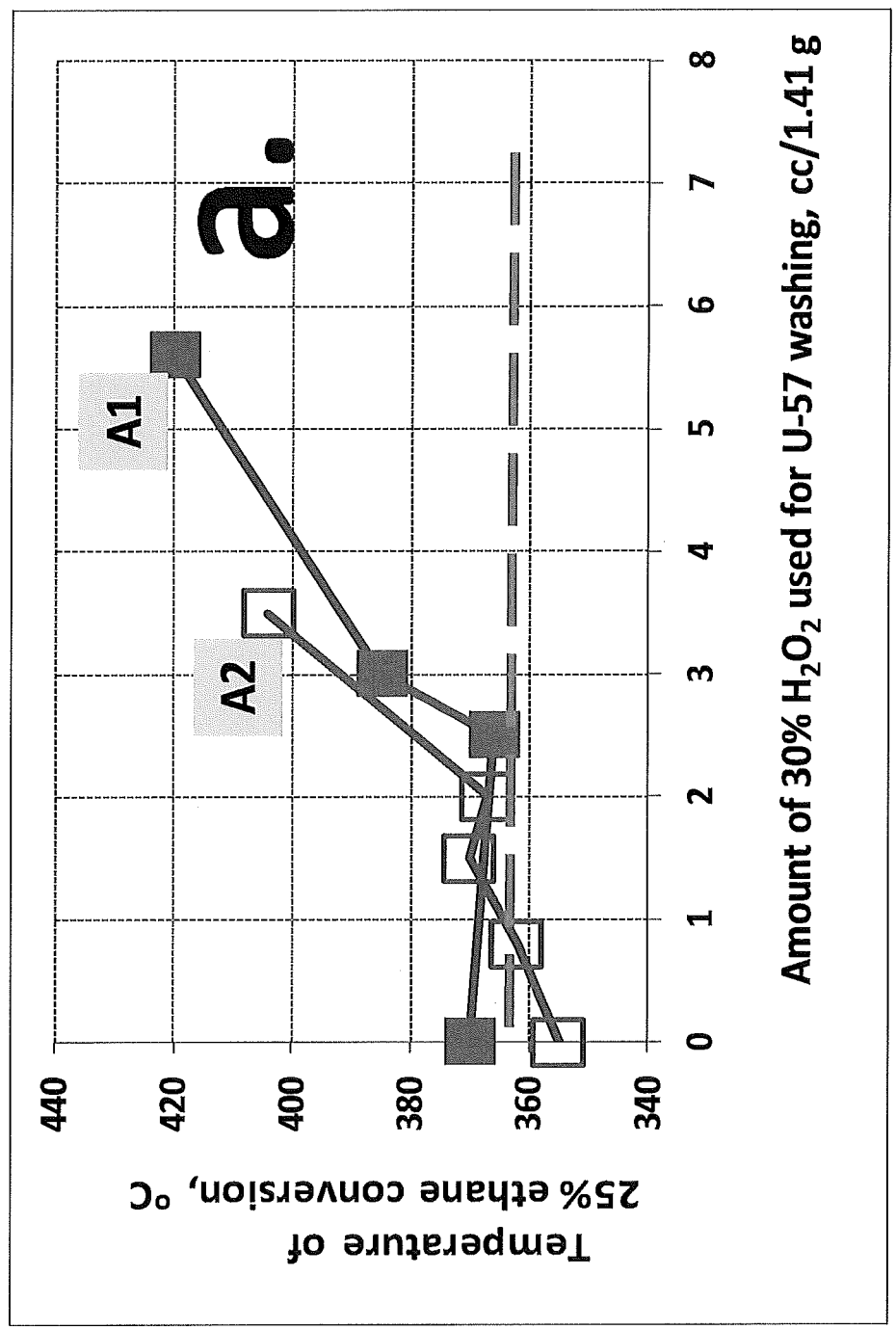
FIG. 2 is a plot of the temperature at which there is a 25% conversion of ethane to ethylene against the volume of 30% $H_2O_2$ for 1.41 g of a catalyst having a temperature at which there is 25% conversion of less than 420° C. and a selectivity to ethylene of greater than 95% prepared in the examples.
Figure 3:
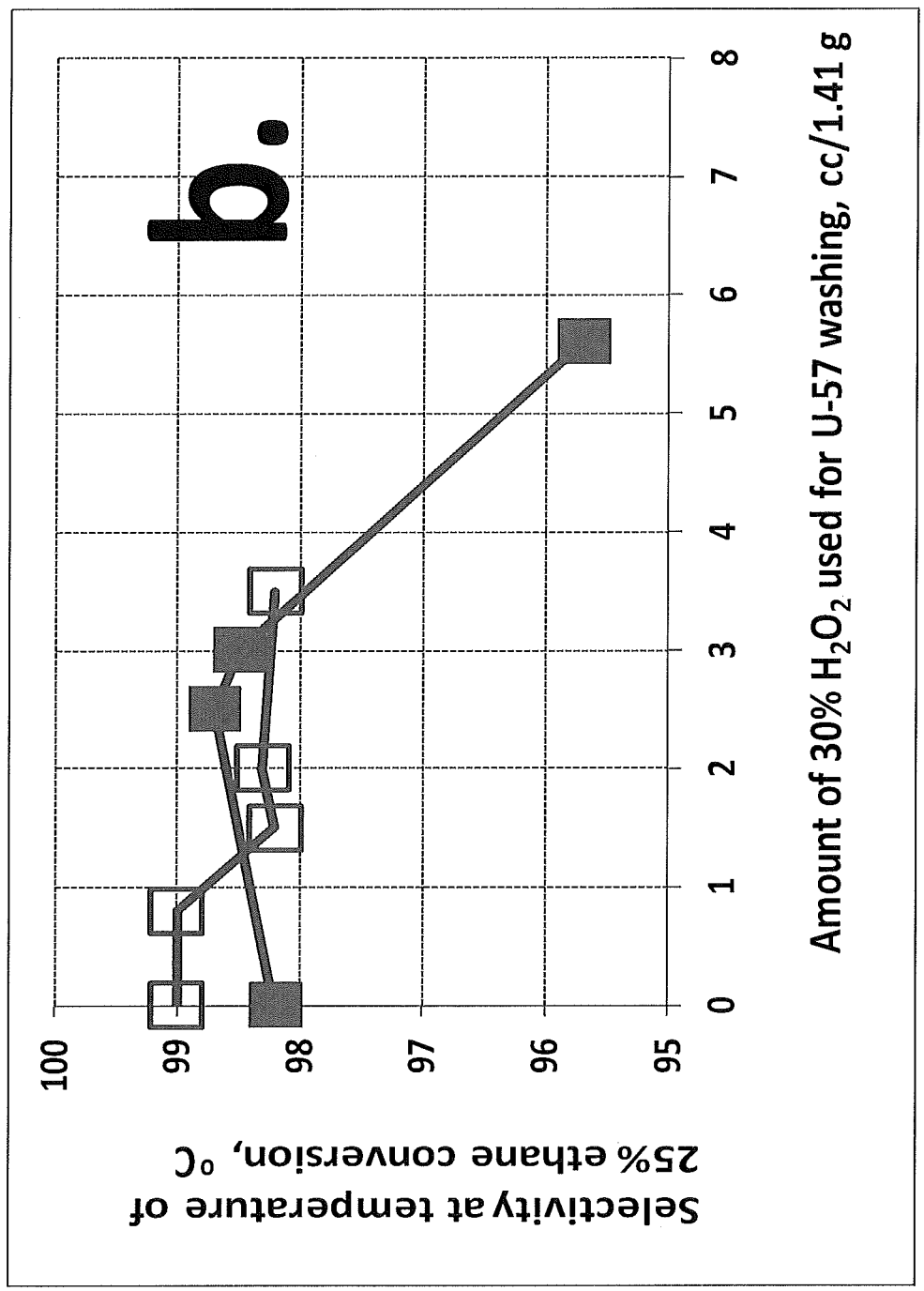
FIG. 3 is a plot of the selectivity for conversion to ethylene at the temperature at which there is a 25% conversion to ethylene against the volume of 30% $H_2O_2$ for 1.41 g of catalyst having a temperature at which there is 25% conversion of less than 420° C. and a selectivity to ethylene of greater than 95% prepared in the examples.

FIG. 2 is a plot of the temperature at which there is a 25% conversion of ethane to ethylene against the volume of 30% $H_2O_2$ for 1.41 g of a catalyst having a temperature at which there is 25% conversion of less than 240° C. and a selectivity to ethylene of greater than 95% prepared at the first laboratory FIG. 3 is a plot of the selectivity for conversion to ethylene at the temperature at which there is a 25% conversion to ethylene against the volume of 30% $H_2O_2$ for 1.41 g of catalyst having a temperature at which there is 25% conversion of less than 240° C. and a selectivity to ethylene of greater than 95% prepared at the first laboratory.

These plots show the volumes of 30% $H_2O_2$ per 1.4 g of catalyst at which catalyst having a temperature at which there is 25% conversion of less than 240° C. and a selectivity to ethylene of greater than 95% is relatively uncompromised up to about 5.6 mL of 30% $H_2O_2$ per 1.4 g of catalyst (i.e. 0.30-2.8 mL $H_2O_2$ of a 30% solution per gram of catalyst).

In the Second Laboratory

Portions of the baseline catalyst precursor prepared as above and treated in a stainless reactor without a TEFLON liner and without seeding were treated with up to from 0.35 to 1.42 mL of 30% w/w $H_2O_2$ aqueous solution per gram of precursor prior to calcining. The treatment of the precursor resulted in an immediate, controlled and observable reaction (bubbling and mild heating which never exceeded about 60° C.).

A series of PIXE characterizations of the base line catalyst and catalyst treated in accordance with the present invention from laboratory two were obtained.

Typical base line untreated catalyst had a PIXE characterization set forth below:

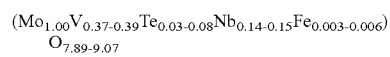

$(Mo_{1.00}V_{0.37-0.39}Te_{0.03-0.08}Nb_{0.14-0.15}Fe_{0.003-0.006})$
$O_{7.89-9.07}$

In base line catalysts treated in an unlined hydrothermal reactor, small amounts of iron and chromium were detected. The iron ranged from a minimum of 0.0026 to a maximum of 0.0416 moles/per mole of Mo. The chromium ranges from 0.000 to 0.0065 moles per mole of Mo.

For catalyst treated in accordance with the present invention prior to calcining, the PIXIE analysis was $(Mo_{1.00}V_{0.28-0.29}Te_{0.13}Nb_{0.15-0.16}Fe_{0.008})O_{8.17}$.

It is believed that these amounts of iron and chromium in catalyst of the above noted base structure do not contribute to the oxidative dehydrogenation characteristics of the catalyst.

Hydrogen peroxide treatment of a catalyst having a temperature at which there is 25% conversion of less than 420° C. and a selectivity to ethylene of greater than 95% prepared in laboratory 2.

Sample 1 A

A catalyst precursor was prepared in the above manner and treated in a stainless steel hydrothermal reactor without a TEFLON liner and without seeding with a catalyst having a temperature at which there is 25% conversion of less than 240° C. and a selectivity to ethylene of greater than 95% was treated with hydrogen peroxide.

5.4672 g of the crude purple catalyst precursor was used for hydrogen peroxide treatment. The catalyst precursor was added to a 400 mL beaker, containing a stir bar, and 20 mL of distilled water was added to create a dark slurry. The slurry was agitated through stirring and 4 mL $H_2O_2$ (30% w/w in $H_2O$; ratio of 1.41 $g_{ODH}$:1 $mL_{H2O2}$) was added all at once and vigorous bubbling and heat resulted. The reaction self-heated and bubbled and changed from dark purple slurry to a black slurry. The reaction was stirred and allowed to proceed for 5 minutes before work up. The solid was filtered, rinsed with approximately 100 mL of water and was dried in an oven at 90° C. overnight to produce 4.4296 g of grey precursor for calcination step. The sample was calcined as above.

Sample 1 C 5.5679 g of the crude purple catalyst precursor was treated in the same manner as Example 1A except that the reaction was allowed to proceed for 2 hours before work up. Some minor bubbling was observed to be arising from the reaction even after a 2 hour reaction time. The solid was filtered (filtrate color was yellow), rinsed with approximately 100 mL of water and was dried in an oven at 90° C. overnight to produce 4.6231 g of vibrant purple precursor for calcination step. The resulting sample was calcined as above.

Sample 1B

A sample of the precursor prepared in a glass flask as above was not treated and calcined as above.

The samples were then used in the oxidative dehydrogenation of ethylene.

The results of the oxidative dehydrogenation test are set out in the table below.

| Sample | Temperature at which 25% conversion was reached, ° C. | Selectivity (%) at 25% conversion |
|---|---|---|
| 1A | 385 | 95 |
| 1B (baseline) | 380 | 95 |
| 1C | 377 | 96 |

Treatment of a precursor for a catalyst having a temperature at which there is 25% conversion of less than 420° C. and a selectivity to ethylene of greater than 95% with 1 mL of 30% $H_2O_2$ per 1.4 g of catalyst precursor does not adversely affect the catalyst.

The samples were then subject to XRD analysis using a Rigaku Ultima X-Ray Diffractometer; 285 mm radius theta/theta goniometer; D/teX-ULTRA High Speed Detector; and ASC-48 Automatic Sample changer. The software used was Data Acquisition Rigaku "Standard Measurement" application; Analysis software MDI Jade 2010 version 2.6.6 2014; and the comparative data base was ICDD PDF-4+2014 (with 354,264 inorganic data patterns).

| Phase | Sample B (base line) % | Sample A % | Sample C % |
|---|---|---|---|
| $(Mo_{0.6}Nb_{0.22}V_{0.18})_5O_{14}$ | 0.0 | 0.0 | 0.0 |
| $(TeO)_{0.71}(Mo_{0.73}V_{0.2}Nb)_{0.07})_3O_9$ | 6.1 | 4.7↓ | 2.8↓ |
| $(TeO)_{0.39}(Mo_{3.52}V_{1.062}Nb)_{0.42})O_{14}$ | 79.0 | 91.8↑ | 95.4↑↑ |
| $V_{0.07}Mo_{0.97}O_5$ | 7.5 | 0.0↓ | 0.0↓ |
| $V_{0.95}Mo_{0.97}O_5$ | 7.5 | 1.4↓ | 0.6↓ |
| $VOMoO_4$ | 1.4 | 1.1 | 0.6↓ |
| $MoS_2$ | 0.6 | 1.0 | 0.6 |

The table suggests that it is desirable to increase the content of the $(TeO)_{0.39}(Mo_{3.52}V_{1.062}Nb)_{0.42})O_{14}$ phase and reduce the content of the $(TeO)_{0.71}(Mo_{0.73}V_{0.2}Nb)_{0.07})_3O_9$ phase.

A further sample of catalyst having a temperature at which there is 25% conversion of less than 420° C. and a selectivity to ethylene of greater than 95% was tested.

Example 2A 7.0552 g of the crude purple catalyst precursor was treated in the same manner as Example 1A except that the reaction was allowed to proceed for 20 minutes before work up. The solid was filtered, rinsed with approximately 100 mL of water and was dried in an oven at 90° C. overnight to produce 5.8907 g of black precursor for calcination step.

Example 2B

Baseline catalyst was not treated.
The results of the oxidative dehydrogenation test are set out in the table below.

| Sample | Temperature at which 25% conversion was reached, ° C. | Selectivity (%) at 25% conversion |
|---|---|---|
| 2A | 399 | 95 |
| 2B (baseline) | 407 | 94 |

Treatment of a precursor for a catalyst having a temperature at which there is 25% conversion of less than 420° C. and a selectivity to ethylene of greater than 95% with 1 mL of 30% $H_2O_2$ per 1.4 g of catalyst precursor does not adversely affect the catalyst.

The samples were then subject to XRD analysis as above.

| Phase | Sample B (base line) % | Sample A % |
|---|---|---|
| $(Mo_{0.6}Nb_{0.22}V_{0.18})_5O_{14}$ | 0.0 | 0.0 |
| $(TeO)_{0.71}(Mo_{0.73}V_{0.2}Nb)_{0.07})_3O_9$ | 15.89 | 6.5↓ |
| $(TeO)_{0.39}(Mo_{3.52}V_{1.062}Nb)_{0.42})O_{14}$ | 72.0 | 93.5↑↑ |
| $V_{0.07}Mo_{0.97}O_5$ | 0.0 | 0.0 |
| $V_{0.95}Mo_{0.97}O_5$ | 12.2 | 0.0↓ |
| $VOMoO_4$ | 0.0 | 0.0 |
| $MoS_2$ | 0.0 | 0.0 |

The treatment with $H_2O_2$ increases the relative proportion of the phase having the structure $(TeO)_{0.39}(Mo_{3.52}V_{1.062}Nb)_{0.42})O_{14}$ and improves the performance of the catalyst.

Examples of treating a catalyst which does not have a temperature at which there is 25% conversion of less than 420° C. and a selectivity to ethylene of greater than 95% with $H_2O_2$

3B

A sample of the catalyst precursor which was calcined without treatment with $H_2O_2$ was tested in the oxidative dehydrogenation reactor. This was the above catalyst that had an estimated temperature for 25% conversion of 504° C.

3A 5.9354 g of the crude purple catalyst precursor for the untreated sample was treated with hydrogen peroxide. The catalyst precursor was added to a 250 mL round bottom flask, containing a stir bar, and 20 mL of distilled water was added to create a dark slurry. The slurry was agitated through stirring and 8.5 mL $H_2O_2$ (30% w/w in $H_2O$; ratio of 0.705 $g_{ODH}$:1 $mL_{H2O2}$) was added all at once and vigorous bubbling and heat resulted. The reaction self-heated and bubbled and changed from dark purple slurry to a black slurry. The reaction was stirred for 2 hours before work up. The dark purple solid was filtered, rinsed with approximately 100 mL of water and was dried in an oven at 90° C. overnight to produce 3.7494 g of grey solid for calcination step.

3C 4.9755 g of the crude purple catalyst precursor was treated as 3A above except 1.75 mL $H_2O_2$ (30% w/w in $H_2O$; ratio 2.82 $g_{ODH}$:1 $mL_{H2O2}$) was added all at once and less bubbling and heat resulted. The reaction slurry remained dark purple. The reaction was stirred for 2 hours before work up. The dark purple solid was filtered, rinsed with approximately 100 mL of water and was dried in an oven at 90° C. overnight to produce 3.8326 g of grey solid for calcination step.

The samples were then tested in the oxidative dehydrogenation reactor. The results are shown in the table below.

| Sample | Temperature at which 25% conversion was reached, ° C. | Selectivity (%) at 25% conversion |
|---|---|---|
| 3A | 386 | 97 |
| 3B (baseline) | 504 | 80 |
| 3C | 390 | 97 |

Treatment of a precursor for a catalyst having a temperature at which there is 25% conversion of greater than 420°

C. and a selectivity to ethylene of less than 95% with 1 mL of 30% $H_2O_2$ per 0.7 to 2.8 g of catalyst precursor significantly improves the catalyst.

The samples were then subject to XRD analysis as above.

| Phase | 3B | 3A | 3C |
|---|---|---|---|
| $(Mo_{0.6}Nb_{0.22}V_{0.18})_5O_{14}$ | 67.1 | 5.8↓↓ | 4.2↓↓ |
| $(TeO)_{0.71}(Mo_{0.73}V_{0.2}Nb)_{0.07})_3O_9$ | 9.8 | 15.0↑ | 0.0↓ |
| $(TeO)_{0.39}(Mo_{3.52}V_{1.062}Nb)_{0.42})O_{14}$ | 9.9 | 76.5↑↑ | 94.3↑↑↑ |
| $VOMoO_4$ | 7.2 | 2.0↓ | 1.5↓ |
| $V_{1.1}Mo_{0.9}O_5$ | 6.0 | 0.7 | 0.0 |

The data suggests that increasing the content of the phase $(TeO)_{0.39}(Mo_{3.52}V_{1.062}Nb)_{0.42})O_{14}$ significantly increases the activity and selectivity of the catalyst.

Example 4

Treatment of the mother liquor with $H_2O_2$ without filtration A sample of precursor was prepared as above. A portion was used as a base line reference (without treatment with $H_2O_2$). Then 4.96 g of the crude purple catalyst precursor and aqueous mother liquor (~500 mL) from hydrothermal treatment was added to a 250 mL round bottom flask, containing a stir bar to create a dark slurry. The dark slurry was kept under nitrogen atmosphere. The slurry was agitated through stirring and 3.6 mL $H_2O_2$ (30% w/w in $H_2O$; ratio of 1.39 $g_{ODH}$:1 $mL_{H2O2}$) was added all at once and no apparent vigorous bubbling and heat resulted. The reaction changed from dark purple slurry to a black slurry. The reaction was stirred for 3 hours before work up. The dark purple solid was filtered, rinsed with approximately 200 mL of water and was dried in an oven at 90° C. overnight to produce 3.3720 g of grey solid for calcination step.

The catalysts were tested for activity in the oxidative dehydrogenation reactor. The results are set forth in the table below.

| Sample | Temperature at which 25% conversion was reached, ° C. | Selectivity (%) at 25% conversion |
|---|---|---|
| 4A | 381 | 96 |
| 4B (baseline) | 437 | 92 |

Treatment of a precursor with 1 $mL_{H2O2}$ (30 wt. %) per 1.4 g of precursor prior to separation from the reactor prior to drying improves the activity of the calcined dehydrogenation catalyst.

Example 5

100 g Sample.

A number of samples of catalysts (approximately 40, 40, and 20 g) were combined into a 5 L round bottom flask and 400 mL of distilled water was added to create a purple slurry. A 100 mL dropper funnel was attached to the flask and 39 mL of $H_2O_2$ (30% wt/wt; ~2.82 $g_{ODH}$/1 $mL_{H2O2}$) was added slowly over 16 minutes dropwise to the stirring slurry. The slurry changed from dark purple to black in color. The solids were filtered, rinsed with DI water and dried at 90° C. in an oven over night. The solids were then ground with a motor and pestle and seized through a 250 micron porosity sifter to collect 101.7 g of a loose and fluffy powder for calcination.

All of the powder was loaded into a quartz tube, which acted as the boat, with some space above to allow gas flow. The quart tube boat was placed inside a larger quartz tube and placed into a unit for calcination. The calcination unit had been thoroughly purged under nitrogen, both bulk and purified to ensure a sufficiently anaerobic environment for calcination. Purified nitrogen flowed over the sample at 150 standard cubic centimeters per minute. The sample was heated from room temperature to 600° C. in 4 hours and held at 600° C. for 4 hours and cooled to room temperature in 4 hours.

A small approximately 2 g sample of the resulting 100 g of catalyst was screened in the oxidative dehydrogenation reactor as described above and it had 25% conversion at 376.5° C. and selectivity to ethylene at this conversion of 97%.

What is claimed is:

1. A method for the oxidative dehydrogenation of a mixed feed comprising ethane and oxygen in a volume ratio from 70:30 to 95:5, wherein the method comprises passing the mixed feed over a calcined oxidative dehydrogenation catalyst of the empirical formula:

$$Mo_{1.0}V_{0.22-0.33}Te_{0.10-0.16}Nb_{0.15-0.19}O_d$$

wherein d is a number to satisfy the valence of the oxide and the empirical formula is determined by PIXE; and wherein the calcined oxidative dehydrogenation catalyst is formed from a catalyst precursor that is treated with $H_2O_2$ and wherein the catalyst precursor is calcined at a temperature from 200° C. to 600° C.

2. The method of claim 1, wherein the gas hourly space velocity greater than 3000 $hr^{-1}$.

3. The method of claim 1, wherein the temperature is less than 400° C.

4. The method of claim 1, wherein the calcined oxidative dehydrogenation catalyst forms a fixed bed in the reactor.

5. The method of claim 1, wherein the gas hourly space velocity is not less than 3000 $hr^{-1}$, the calcined oxidative dehydrogenation catalyst forms a fixed bed in the reactor, and the selectivity to ethylene is not less than 90%.

6. The method according to claim 1, wherein the calcined oxidative dehydrogenation catalyst has the empirical formula:

$$Mo_{1.0}V_{0.22-0.29}Te_{0.10-0.16}Nb_{0.15-0.19}O_d$$

wherein d is a number to satisfy the valence of the oxide and the empirical formula is determined by PIXE.

7. The method according to claim 1, wherein the calcined oxidative dehydrogenation catalyst has the empirical formula:

$$Mo_{1.0}V_{0.22-0.29}Te_{0.11-0.15}Nb_{0.15-0.19}O_d$$

wherein d is a number to satisfy the valence of the oxide and the empirical formula is determined by PIXE.

8. The method of claim 1, wherein the calcined oxidative dehydrogenation catalyst has a bulk density from 1.20 g/cc to 1.53 g/cc.

9. The method of claim 1, wherein, in the crystalline phase of the calcined oxidative dehydrogenation catalyst, the amount of the phase having the formula
   $(TeO)_{0.39}(Mo_{3.52}V_{1.06}Nb_{0.42})O_{14}$ is above 75 wt. % of the measured crystalline phase as determined by XRD.

10. The method of claim 1, wherein, in the crystalline phase of the calcined oxidative dehydrogenation catalyst, the amount of the phase having the formula
   $(TeO)_{0.39}(Mo_{3.52}V_{1.06}Nb_{0.42})O_{14}$ is above 85 wt. % of measured crystalline phase as determined by XRD.

* * * * *